United States Patent [19]

Dragsten et al.

[11] Patent Number: 5,847,110
[45] Date of Patent: Dec. 8, 1998

[54] METHOD OF REDUCING A SCHIFF BASE

[75] Inventors: Paul R. Dragsten, Chanhassen; Gregory J. Hansen, Fridley, both of Minn.

[73] Assignee: Biomedical Frontiers, Inc., Minneapolis, Minn.

[21] Appl. No.: 911,991

[22] Filed: Aug. 15, 1997

[51] Int. Cl.⁶ .......................... C08B 30/00; C08B 37/00; C08B 37/02; C07C 209/00
[52] U.S. Cl. .................... 536/124; 536/17.9; 536/18.5; 536/18.7; 536/102; 536/112; 536/123.1; 564/123; 564/488; 564/489
[58] Field of Search .................... 536/17.9, 18.5, 536/18.7, 102, 112, 123.1, 124; 564/8, 123, 489, 488

[56] References Cited

U.S. PATENT DOCUMENTS

| | | | |
|---|---|---|---|
| 3,706,633 | 12/1972 | Katchalski et al. | 195/63 |
| 4,217,338 | 8/1980 | Quash | 424/1 |
| 4,419,444 | 12/1983 | Quash | 435/7 |
| 4,699,784 | 10/1987 | Shih et al. | 424/85 |
| 4,975,533 | 12/1990 | Kondo et al. | 536/55.3 |
| 5,057,313 | 10/1991 | Shih et al. | 424/85.91 |

OTHER PUBLICATIONS

Pelter, A. et al., "Reductive Aminations of Ketones and Aldehydes using Borane–Pyridine", *J. Chem. Soc.*, Perkins Trans. 1, pp. 717–720 (1984).

*Primary Examiner*—Howard C. Lee
*Attorney, Agent, or Firm*—Merchant, Gould, Smith, Edell, Welter & Schmidt, P.A.

[57] ABSTRACT

The invention relates to methods of reducing Schiff bases and making chelator conjugates by treating with borane-pyridine complex.

47 Claims, No Drawings

METHOD OF REDUCING A SCHIFF BASE

BACKGROUND OF THE INVENTION

Schiff bases can be reduced by a variety of known reducing agents, for example, sodium borohydride, sodium cyanoborohydride, and the like. However, selective reduction of Schiff bases in molecules with other functional groups remains problematic. It is particularly difficult to selectively reduce Schiff bases in an aqueous solvent. For example, selective reduction of Schiff bases in a water soluble macromolecule at an acceptable yield has been difficult to achieve.

Amine complexes of borane are a family of reducing agents that have been shown to have broad reactivity under a variety of conditions. For example, borane-amine complexes can reduce carbonyl compounds in a variety of solvents. Typically though, borane-amine complexes are much more effective reducing agents in strong aqueous acid, such as a mineral acid or a Lewis acid, than in water. Mild conditions for reduction with borane-amine complexes include use of glacial acetic acid as a solvent, and borane-amine complexes reduce Schiff bases in glacial acetic acid.

In glacial acetic acid, borane-pyridine complex causes reductive amination of aldehyde or ketone and reduction of Schiff bases. Introduction of polar or hydrophilic cosolvents typically reduces or eliminates reduction of a Schiff base. Furthermore, some Schiff bases are reduced less readily than others. Although borane-pyridine complex was found to be effective for reducing Schiff bases formed from acetophenone or benzaldehyde, it was not effective in reducing Schiff bases derived from more hindered or less reactive ketones. For example, yields as high as 93% were obtained for reductive amination of acetaldehyde or cyclohexanone, but no reduction was observed when the Schiff base was derived from the reaction of aniline with camphor or of acetophenone with a hindered amine such as octylamine or cyclohexylamine.

Given the shortcomings of the current methods for reducing Schiff bases described above, a need exists for a method to reduce Schiff bases in aqueous solvents, in the presence of carbonyl groups, on unreactive molecules, or on hindered molecules, such as a water soluble carrier.

SUMMARY OF THE INVENTION

The present invention relates to a method for reducing a Schiff base and meets the needs described above. The method includes treating a Schiff base with borane-pyridine complex (or borane-pyridine) in an aqueous solution at a non-acid pH, such as pH at least about 4. The method can also include one or more steps for making the Schiff base, such as oxidizing a water soluble carrier to form a modified water soluble carrier comprising a dialdehyde moiety, and/or reacting a modified water soluble carrier with an amine to form the Schiff base.

This embodiment of the invention can also include additional steps, such as reducing aldehyde present after treating a Schiff base with borane-pyridine complex. This reduction can be accomplished by treating with sodium borohydride.

Products of and reactants in the method can be purified as part of the method. For example, purifying the Schiff base or the treated Schiff base can be accomplished by a method such as diafiltering or diafiltration.

In another embodiment of the invention, the method makes a covalently bonded conjugate of an amine and a water soluble carrier. In this embodiment the method includes steps of reacting a water soluble carrier with an amine, and treating reacted water soluble carrier with borane-pyridine complex.

This embodiment of the invention can also include additional steps, such as modifying a water soluble carrier to introduce groups that react with an amine and/or reducing species present after the treating step. A water soluble carrier can be modified by, for example, oxidation or reaction with a linking group to produce or incorporate carbonyl groups on the water soluble carrier. The reduction can be accomplished by treating with sodium borohydride.

The water soluble carrier, the initial product from reacting water soluble carrier with amine, the product from treating with borane-pyridine complex, or any other form of the water soluble carrier can be purified as part of the method. Purifying includes procedures such as diafiltering. Purifying also includes purifying the conjugate into a pharmaceutically acceptable vehicle.

The present invention also includes products of the methods of the invention. These products include a reduced Schiff base produced by a process including the step of treating the Schiff base with borane-pyridine complex in an aqueous solution at a non-acid pH, such as pH at least about 4. Another product of the methods of the invention includes a covalently bonded conjugate of an amine and a water soluble carrier produced by a process including the steps of reacting a water soluble carrier with an amine, and treating the reacted water soluble carrier with borane-pyridine complex.

The water soluble carrier of the invention is preferably a large molecule that has characteristics such that conjugating a chelator with the water soluble carrier results in desirable biological properties such as increasing efficacy, prolonging the circulating half-life, decreasing toxicity, and the like. Preferably, the water soluble carrier is a polysaccharide, for example, starch, a starch derivative, dextran, or hyaluronic acid. In a preferred embodiment, the water soluble carrier is hydroxyethyl starch.

Advantageously, the amine of the invention is a chelator. Preferably the chelator is effective to chelate iron so that the iron can be excreted from the body of a patient. In a preferred embodiment, the chelator is deferoxamine.

In a preferred embodiment, a conjugate of deferoxamine with hydroxyethyl starch (HES-DFO) is effective to decrease iron load in a patient suffering from an iron overload disorder. Preferably, the conjugate of the invention can be administered to a patient without unacceptable adverse side effects.

Preferably, a chelator conjugate of the invention can be formulated as a solution, suspension, or emulsion, or similar liquid based form, preferably in a formulation suitable for administration to a patient. Preferably, the chelator conjugate is formulated in a pharmaceutically accepted vehicle. Preferably, the pharmaceutically acceptable vehicle is water including about 0.9% sodium chloride or lactated Ringer's solution. Preferably, the chelator conjugate is formulated as a solution with chelator conjugate concentration of about 5 g/L to about 250 g/L. Preferably, the chelator conjugate is administered as a solution with a total chelator concentration of about 5 mM to about 250 mM.

DETAILED DESCRIPTION OF THE INVENTION

Reducing Schiff Bases With Borane-Pyridine Complex

Although previous methods for reducing Schiff bases with borane complexes require an acidic, non-aqueous solvent such as glacial acetic acid, reduction of Schiff bases with borane-pyridine complex can be accomplished in an aqueous solution at a non-acid pH, such as pH at least about 4. The present method can specifically reduce a Schiff base in an aqueous solvent in the presence of a dialdehyde without substantially reducing the dialdehyde. Such a specific reduction can be readily accomplished by treating the Schiff base with borane-pyridine complex. Treatment with borane-pyridine complex is also useful to make a stable, covalently bonded conjugate of an amine and a water soluble carrier. The water soluble carrier is reacted with an amine, and then the product of this reaction is treated with borane-pyridine complex. Prior to reaction with the amine, the water soluble carrier can be modified to introduce groups that will react with an amine.

The reaction of borane-pyridine complex with a Schiff base and the reaction of borane-pyridine complex in forming a covalently bonded conjugate of an amine and water soluble carrier proceed in moderate to high yield. Borane-pyridine complex at a concentration of about 50 mM can reduce nearly an equivalent of Schiff base. For example, 50 mM borane-pyridine complex can reduce about 20 mM to about 40 mM, preferably about 25 mM to about 35 mM, preferably about 26 mM to about 30 mM of Schiff base. Preferred concentrations of borane-pyridine complex are about 75 mM to about 200 mM.

The method is effective for reducing Schiff bases at the wide range of concentrations of Schiff base encountered in reactions described herein. The method is effective for reducing a wide range of concentrations of covalent adducts of an amine and a water soluble carrier, for example about 5 mM to about 200 mM. Typically, the total concentration of all forms of the water soluble carrier is about 5 g/L to about 250 g/L, preferably about 100 g/L to about 200 g/L.

Such reactions can be run in, and the stated yields are achieved in, an aqueous solution including, for example, a salt, an alcohol, and the like. Preferably the pH of the aqueous solution is at least about 4. Advantageously, the reaction is run in an aqueous solution at pH about 4 to about 7.5, preferably pH about 5 to about 6. Salts may be present in the reaction mixture to maintain the ionic strength or as a result of pH adjustment. An alcohol, such as ethanol, can be added to the reaction of Schiff base with borane-pyridine complex. Ethanol can be present at up to about 50 weight percent (wt %), preferably about 10 to about 40 weight percent, preferably about 10 to about 30 weight percent.

Reactions can be run at bench top conditions such as at room temperature with stirring. Temperature is preferably about 15° C. to about 40° C., preferably about 20° C. to about 25° C. Typical reaction times are in the range of hours, for example, up to about 30 hours, preferably about 15 to about 25 hours, preferably about 20 hours. No special precautions need be taken regarding maintaining an inert atmosphere, sealing the reaction vessel, and the like.

Forming Schiff Bases

A variety of Schiff bases can be reduced in aqueous solution using borane-pyridine complex. A Schiff base can be produced in situ or produced in another reaction and, optionally, purified prior to reduction with borane-pyridine complex. A Schiff base can even be obtained from commercial sources. A variety of different aldehydes or ketones and amines form Schiff bases suitable for treating with borane-pyridine complex.

Aldehyde or ketone

A variety of aldehydes and ketones can be used to make a Schiff base or conjugate. An aldehyde or ketone can be formed in situ or can be formed in another reaction and, optionally, purified prior to reaction with an amine and reduction with borane-pyridine complex. A preferred aldehyde or ketone includes a water soluble aldehyde or ketone such as a natural or a modified water soluble carrier.

The water soluble carrier is preferably a natural polymer, a modified natural polymer, or another pharmaceutically acceptable organic polymer. Such water soluble carriers include polysaccharides such as dextrans and hyaluronic acid, starch and starch derivatives, and proteins such as human serum albumin, and the like. Polymer starting materials such as the dextrans, human albumin and plasma protein fraction are commercially available as water-soluble preparations or as solutions. See *Remington's Pharmaceutical Sciences,* A. Osol., ed., Mack Publishing (16th ed. 1980) at pages 759–761. Water soluble carriers of the invention include those described in U.S. Pat. Nos. 4,863,964, 5,217,998, and 5,268,165, and U.S. patent application Ser. No. 08/745,335, filed Nov. 8, 1996, the disclosures of which are incorporated herein by reference.

The water soluble carrier is preferably sufficiently stable to carry a chelator in a patient for a sufficient time that it is effective to treat an iron overload disorder. In addition, the water soluble carrier is typically sufficiently well-tolerated and non-toxic that the patient has no unacceptable adverse reactions to administration of the water soluble carrier. Preferably, a conjugate of water soluble carrier with a chelator has fewer side effects and lower toxicity than the chelator alone.

The water soluble carrier can be modified to incorporate aldehyde or ketone moieties for formation of a Schiff base. For example, a carbohydrate can be oxidized to form a dialdehyde. Alternatively, aldehyde or ketone moieties can be introduced into a water soluble carrier by derivatizing the water soluble carrier with a reagent, such as a linking reagent, that contains aldehyde or ketone moieties.

Aldehydic groups can be introduced into the polymer substrates by known techniques, e.g. by the oxidation of carbohydrates or other diols to dialdehydes with sodium metaperiodate. See, for example, M. B. Wilson, et al. in *Immunofluorescence and Related Staining Techniques,* W. Knapp et al., eds., Elsevier/North Holland Biomedical Press (1978) at page 215', Flemming et al., *Acta Biol. Med. Ger.,* 30, 177 (1973); and, S. -C. Tam et al., in *P.N.A.S. U.S.A.,* 73, 2128 (1976).

Amines

A variety of amines can be used to form Schiff bases for reduction with borane-pyridine complex in aqueous solvents. Advantageously, the amine will react with the water soluble carrier to form a Schiff base, which when reduced, results in a desirable characteristic or property being imparted to the water soluble carrier. For example, preferred amines are chelators.

Preferred chelators are useful, by themselves or as conjugates, in treating iron overload disorders. Iron chelators that have been studied in the treatment of iron overload disorders include deferoxamine (deferrioxamine or desferrioxamine), 2,3-dihydroxybenzoic acid, DTPA, rhodotorulic acid, cholylhydroxamic acid, ethylene diamine-$N,N^1$-bis(2-hydroxyphenylacetic acid), isoniazid-pyridoxal hydrozone, 1,2-dimethyl-3-hydroxypyrid-4-one and nitrilotriacetate. These chelators can be used alone or in combination.

A preferred chelator conjugate can be prepared by covalently bonding deferoxamine to a pharmaceutically-acceptable organic polymer or water soluble carrier. Methods for the preparation of deferoxamine (N-[5-[3[(5-aminopentyl) hydroxycarbamoyl] propionamido]pentyl]-3-[[5-(N-hydroxyacetamido) pentyl] carbamoyl] propionohydroxamic acid) and its pharmaceutically-acceptable salts have been disclosed, e.g., by Prelog et al., in *Helv. Chim. Acta.*, 45, 631 (1962); Bickel et al., *Helv. Chim. Acta.* 46 1385 (1963); in German Pat. Spec. 1,186,076 and in U.S. Pat. Nos. 4,419,365, 4,987,253, and 5,493,053, the disclosures of which are incorporated by reference herein. Such salts include the acid addition salts of methane sulfonic acid, phosphoric acid, acetic acid, lactic acid, tartaric acid, citric acid, hydrochloric acid, and the like.

Methods for preparing Schiff bases or adducts of amines with water soluble carriers of the invention include the methods described in U.S. Pat. Nos. 4,863,964, 5,217,998, 5,268,165, and U.S. patent application Ser. No. 08/745,335, filed Nov. 8, 1996, the disclosures of which are incorporated herein by reference.

The mole ratio of deferoxamine/water soluble carrier attained using reactions with carboxyl or carbonyl groups can vary widely, depending on factors such as the number of reactive groups on the polymer, steric hindrance, rate and extent of Schiff base or amide formation, and the like. More than one molecule of chelator can be attached to each molecule of water soluble carrier. As an example, about 0.6–0.7 g of deferoxamine can be bonded to about 2.5 g of reacted Dextran 40, via reaction of the deferoxamine with aldehyde groups introduced into the dextran, followed by reduction. When the water soluble carrier is hydroxyethyl starch, about 0.2 g to about 1.2 g of deferoxamine can be bonded to about 1 g of hydroxyethyl starch.

Preferably, when the chelator is deferoxamine, the water soluble carrier is hydroxyethyl starch. More preferably, the hydroxyethyl starch has an average molecular weight of between about 50 kD and about 200 kD as measured by gel permeation chromatography using Pullulan molecular weight standards. The corresponding average molecular weights determined using light scattering methods are about 50 kD to about 300 kD.

Reduction of Remaining Carbonyl Groups

One feature of the present invention is that a Schiff base can be reduced selectively, that is, without an undesired or substantial reduction of aldehyde or ketone groups that may be present in the reaction mixture. For example, Schiff bases can be reduced in aqueous solution using borane-pyridine complex without substantially reducing a dialdehyde that is also present. In the context of the extent of reduction of aldehyde or ketone groups that may be present in the reaction mixture, without substantially reducing, not reducing, or a lack of reduction refer to an extent of reduction that is at a suitable extent less than the degree of reduction of the Schiff base. For example, in some circumstances the reduction of the Schiff base is a slow reaction and reduction of any aldehyde or ketone groups that may be present in the reaction mixture is advantageously slow, or occurs to a small extent, compared to the reduction of the Schiff base. For example, insubstantial reduction of aldehyde or ketone can be reduction of less than about 30%, preferably less than about 20%, preferably less than about 10% of the aldehyde or ketone present, when, for example, about 50 to about 75% of the Schiff base is reduced.

In many circumstances it is desirable to reduce an aldehyde or ketone group that does not form a Schiff base. Such reduction can be accomplished prior to use of or by further processing of a product containing reduced Schiff base. Reduction of remaining aldehyde or ketone groups can be accomplished using any suitable reagent. When the Schiff base or the aldehyde or ketone group occurs on a water soluble carrier, sodium borohydride is a suitable reducing agent for unreacted aldehyde or ketone groups. For example, unreacted aldehyde or ketone groups in periodate oxidized hydroxyethyl starch can be reduced by treatment with about 100 mM to about 300 mM, preferably about 200 mM to about 300 mM, preferably about 225 mM sodium borohydride with stirring for up to about 4 hours.

Purification of Reagents and Products

A reagent or product used in the method of the invention can be purified before use and/or after reaction, reduction or treatment in the method of the invention. Such purification can be accomplished by methods standard in the art. For example, a water soluble carrier, Schiff base, treated Schiff base, or covalent conjugate can be purified by diafiltration. Other suitable methods for purification of water soluble carriers and the like include size exclusion chromatography, hydrophobic interaction chromatography, ion exchange chromatography, and like methods.

Methods for purifying a water soluble carrier or chelator conjugate of the invention include the methods described in U.S. Pat. Nos. 4,863,964, 5,217,998, 5,268,165, and U.S. patent application Ser. No. 08/745,335, filed Nov. 8, 1996, the disclosures of which are incorporated herein by reference.

Borane-pyridine complex can be used directly as obtained from the supplier. Additional reagents that can be used as obtained from the supplier include deferoxamine, hydroxyethyl starch, dextran, and the like.

When the different reactions of the Schiff base or the covalent conjugate of an amine and a water soluble carrier are complete, purification can be used to place a product in the desired solvent or vehicle. For example, it may be desirable to have a reduced Schiff base in another solvent for further processes or uses. Advantageously, a covalent conjugate of a chelator and a water soluble carrier can be purified into a pharmaceutically acceptable vehicle. Pharmaceutically acceptable vehicles are known to those of skill in the art and include water for injection, pyrogen free water, isotonic buffered salt solutions, water including about 0.9% sodium chloride, water for injection including about 0.9% sodium chloride, and lactated Ringer's solution.

Product of Reduction of Schiff Bases with Borane-Pyridine Complex

Reduction of a Schiff base yields a substituted amine. Reduction of a Schiff base, or other adduct, formed between a chelator and a water soluble carrier forms a stable covalent conjugate of the chelator and the water soluble carrier. Using the method of the invention this can be accomplished in a manner where the chelating ability, as measured in vitro, remains substantial, and preferably on the order of the non-conjugated chelator.

Preferred preparations of chelator conjugates for use in vivo provide preferred characteristics for pharmaceutical use. Chelator conjugate preferably is sufficiently soluble for ease of introduction or administration. The chelating moiety of the chelator conjugate is effective as a chelator, even in vivo. Preferred chelator conjugate shows improved vascular retention and is efficacious in generating iron excretion from animals. Preferred chelator conjugate is not substantially toxic, at least at or near therapeutic levels, and preferably not within about 5 to 10 times therapeutic levels. The preferred water soluble carrier does not cause significant side reactions, and thus is selected from polymers which are biocompatible.

Preferably, the chelator conjugate is soluble in aqueous solution at a concentration of about 5 g/L to about 250 g/L. Such a solution will include a total chelator concentration of about 5 mM to about 250 mM.

The invention will be further described by reference to the following detailed examples, which are illustrative of but not limiting to the present invention.

EXAMPLES

Example 1

Reduction of Schiff Base with Sodium Borohydride

A Schiff base was formed by reaction of oxidized hydroxyethyl starch with deferoxamine. Hydroxyethyl starch was dissolved in water for injection at 100 g/L. Sodium periodate, 100 mM, was added to oxidize the hydroxyethyl starch and form dialdehyde. The reaction mixture was subjected to diafiltration against approximately five volumes of water for injection to remove low molecular weight species from the hydroxyethyl starch. The oxidized hydroxyethyl starch was at about 100 g/L. Deferoxamine was added to the solution of oxidized hydroxyethyl starch to a final concentration of 75 mM and this mixture was stirred for 1 hr at room temperature.

Then $NaBH_4$ was added to yield a final concentration of $NaBH_4$ of 150 mM and the reaction was allowed to proceed with stirring for 20 hours. The reduction reaction was run at pH 8.5 and room temperature. This reaction mixture was then diafiltered against approximately 10 volumes of purified water to remove low molecular weight species from the hydroxyethyl starch conjugate. At this point, the pH and concentration of the solution of hydroxyethyl starch conjugate was adjusted, and sodium chloride was added to bring the product to isotonicity.

The yield of conjugate product was determined in two ways. First, a concentration of chelator attached to the polymer at a polymer concentration of 100 g/L was determined. This was accomplished by saturating the chelator with iron, followed by gel permeation, chromatography and detecting and quantifying the iron-saturated chelator spectrophotometrically. The high molecular weight chelator concentration produced by $NaBH_4$ was 3 mM. Second, the yield of chelator attached to the hydroxyethyl starch as a percentage of the total chelator added to the reaction vessel was determined. This was determined from the quantity of conjugated chelator divided by the number of moles of chelator added to the reaction mixture. Reaction with $NaBH_4$ yielded only 4% of the chelator attached to hydroxyethyl starch.

Example 2

Reduction of Schiff Base with Sodium Cyanoborohydride

Reduction with sodium cyanoborohydride was accomplished by the general procedure of Example 1, with the following exceptions. Sodium cyanoborohyride was added after deferoxamine. The concentration of sodium cyanoborohydride in the reaction mixture was 50 mM, and the pH of the reaction was 7. After 20 hours of reduction with sodium cyanoborohydride, sodium borohydride is added to a concentration of 150 mM to reduce unreacted aldehydes. After addition of sodium borohydride, the reaction was stirred for about 4 hours. Then the hydroxyethyl starch conjugate was subjected to diafiltration as described above.

The yield of hydroxyethyl starch conjugate from reduction with sodium cyanoborohydride was determined by the general procedures of Example 1. The high molecular weight chelator concentration was 26 mM. The chelator attachment yield was 36%. These values represent an approximately 9-fold improvement over reduction with $NaBH_4$.

In another experiment, reduction with sodium cyanoborohydride was done as described above, but with a 20 hour incubation at pH 5. This pH 5 reaction yielded high molecular weight chelator concentration was 27 mM. The chelator attachment yield was 39%.

In a third trial, the reduction reaction was run under the conditions described above at pH 7, but with 75 mM sodium cyanoborohydride. The high molecular weight chelator concentration was about 28 mM and the chelator attachment yield was about 34%.

Example 3

Reduction of Schiff Base with Borane-Dimethylamine Complex

Reduction of a Schiff base with borane-dimethylamine complex was accomplished by the general procedure of Example 2, with the following exceptions. The borane dimethylamine complex was added to a concentration of 50 mM, and the reduction was run at pH 7 for 19 hours.

Yield of conjugate of hydroxyethyl starch and chelator was determined generally as described in Example 1. High molecular weight chelator concentration was 8 mM. The chelator attachment yield was 11%. Although this yield was better than that obtained with $NaBH_4$, it is well below that obtained with sodium cyanoborohydride.

Example 4

Reduction of Schiff Base with Borane-Trimethylamine Complex

Reduction of Schiff base was accomplished generally as described in Example 2, with the following exceptions. Borane-trimethylamine complex was added to a final concentration of 50 mM and the reaction mixture was stirred for 26 hours at pH 7.

The yield of the hydroxyethyl starch-chelator conjugate was determined generally as described in Example 1. The high molecular weight chelator concentration was 8 mM. The chelator attachment yield was 11%. Like borane-dimethylamine complex, borane-trimethylamine complex gave yields greater than those with $NaBH_4$, but less than the yield with sodium cyanoborohydride.

In another trial with borane-trimethylamine complex, the reduction reaction was run as described above, but the reaction proceeded for 20 hours at pH 4–5. This reaction resulted in a high molecular weight chelator concentration of 6 mM and a chelator attachment yield of 8%. This low pH treatment with borane-trimethylamine complex results in a yield intermediate between the other complexes of borane with trimethylamine or dimethylamine and the yield with $NaBH_4$.

Example 5

Reduction of Schiff Base with Borane-Pyridine Complex

Experiment 1

The procedure for reduction of Schiff base is generally the same as that of Example 2, with the following differences.

After diafiltration of the oxidized hydroxyethyl starch, the solution was diluted with ethanol and water to bring the concentration of hydroxyethyl starch to 100 g/L and the volume fraction of ethanol to 30%. Deferoxamine was added to a concentration of 75 mM. Borane-pyridine complex was then added to a final concentration of 100 mM and the reaction mixture was stirred for 20 hours at pH 5.5.

The yield of conjugate of hydroxyethyl starch with chelator was determined generally as described in Example 1. The high molecular weight chelator concentration was 33 mM. The chelator attachment yield was 47%.

Experiment 2

Experiment 2 generally followed the procedures of Experiment 1, except the concentration of borane-pyridine complex in the reduction reaction was 50 mM. The high molecular weight chelator concentration resulting from this reaction was 31 mM and the chelator attachment yield was 41%.

Experiment 3

Experiment 3 generally followed the procedures of Experiment 1, except the concentration of deferoxamine was 35 mM. The reduction reaction resulted in a high molecular weight chelator concentration of 26 mM and a chelator attachment yield of 85%. This is the highest yield of conjugate of any of the examples.

Experiment 4

Experiment 4 generally followed the procedures of Experiment 1, except the concentration of hydroxyethyl starch was 150 g/L, the concentration of deferoxamine was 113 mM, and the concentration of borane-pyridine complex was 150 mM. The high molecular weight chelator concentration resulting from this reaction was 35 mM and the chelator attachment yield was 55%.

Experiment 5

Experiment 5 generally followed the procedures of Experiment 1, except the concentration of borane-pyridine complex in the reduction reaction was 50 mM. The high molecular weight chelator concentration resulting from this reaction was 31 mM and the chelator attachment yield was 41.

Experiment 6

Experiment 6 generally followed the procedures of Experiment 1, except the concentration of periodate was 100 mM, hydroxyethyl starch was at 150 g/L, borane-pyridine complex was at 150 mM, and deferoxamine was at 113 mM. The reduction reaction resulted in a high molecular weight chelator concentration of 40 mM and a chelator attachment yield of 68%.

Discussion

Reduction of Schiff base to form a stable, covalent conjugate of a chelator and a water soluble carrier using borane-pyridine complex is advantageous compared to reduction with other reducing agents. Yields are much higher compared to sodium borohydride or to complexes of borane with dimethylamine or trimethylamine. Compared to cyanoborohydride, yields are nearly double. In addition, reduction with cyanoborohydride yields cyanide, which must be thoroughly removed from a therapeutic chelator conjugate before use of the chelator conjugate. Additional advantages over reduction with cyanoborohydride include the ability to maintain the pH at about 5.5 without buffering. This is believed to reduce polymer breakdown during reduction of the Schiff base.

The invention has been described with reference to various specific and preferred embodiments and techniques. However, it should be understood that many variations and modifications may be made while remaining within the spirit and scope of the invention. All publications and patent applications in this specification are indicative of the level of ordinary skill in the art to which this invention pertains.

We claim:

1. A method of reducing a Schiff base, the method comprising the step of:

reducing the Schiff base with borane-pyridine complex in an aqueous solvent with pH at least about 4.

2. The method of claim 1, wherein the Schiff base is formed from an amine and a dialdehyde.

3. The method of claim 2, further comprising, before reducing the Schiff base, the step of:

forming the dialdehyde by oxidizing a water soluble carrier to form a modified water soluble carrier comprising a dialdehyde moiety.

4. The method of claim 3, wherein the water soluble carrier is a polysaccharide.

5. The method of claim 4, wherein the water soluble carrier is starch, a starch derivative, dextran, or hyaluronic acid.

6. The method of claim 1, further comprising, before reducing the Schiff base, the step of:

forming the Schiff base by reacting a modified water soluble carrier with an amine.

7. The method of claim 6, wherein the water soluble carrier is a modified polysaccharide.

8. The method of claim 7, wherein the modified water soluble carrier is modified starch, a starch derivative, modified dextran, or modified hyaluronic acid.

9. The method of claim 6, wherein total concentration of any form of the water soluble carriers is about 5 g/L to about 250 g/L.

10. The method of claim 6, wherein the amine is a chelator.

11. The method of claim 10, wherein the chelator is deferoxamine.

12. The method of claim 1, further comprising, before reducing the Schiff base, the step of:

purifying the Schiff base.

13. The method of claim 1, further comprising, after reducing the Schiff base, the step of:

reducing remaining aldehyde.

14. The method of claim 13, wherein the step of reducing comprises treating with sodium borohydride.

15. The method of claim 1, further comprising, after reducing the Schiff base, the step of:

purifying the reduced Schiff base.

16. The method of claim 15, wherein the step of purifying comprises diafiltering the treated Schiff base.

17. The method of claim 1, wherein the aqueous solvent is about 70 weight percent to about 90 weight percent purified water and about 0 weight percent to about 30 weight percent ethanol.

18. The method of claim 1, wherein the pH is about 4 to less than about 7.5.

19. The method of claim 1, wherein the pH is about 5 to about 6.

20. The method of claim 1, wherein the treating step lasts about 15 to about 25 hours.

21. The method of claim 1, wherein the treating step is at a temperature of about 15° C. to about 40° C.

22. The method of claim 1, wherein the borane-pyridine complex is at a concentration of about 75 mM to about 200 mM.

23. A method for making a covalently bonded conjugate of an amine and a water soluble carrier, the method comprising the steps of:

reacting a water soluble carrier with an amine; and reducing the reacted water soluble carrier with borane-pyridine complex at a pH at least about 4.

24. The method of claim 23, further comprising, before the reacting step, the step of:

modifying the water soluble carrier to form groups that react with an amine.

25. The method of claim 24, wherein the water soluble carrier is a polysaccharide.

26. The method of claim 25, wherein the water soluble carrier is starch, a starch derivative, dextran, or hyaluronic acid.

27. The method of claim 26, wherein the water soluble carrier is hydroxyethyl starch.

28. The method of claim 27, wherein the hydroxyethyl starch has an average molecular weight of about 50 kD to about 200 kD.

29. The method of claim 23, wherein the amine is a chelator.

30. The method of claim 29, wherein the chelator is deferoxamine.

31. The method of claim 23, further comprising, after reducing with borane-pyridine complex, the step of:

reducing remaining aldehyde.

32. The method of claim 31, wherein the step of reducing comprises treating with sodium borohydride.

33. The method of claim 23, further comprising, after reducing with borane-pyridine complex, the step or steps of:

purifying any form of the water soluble carrier or covalent conjugate.

34. The method of claim 33, wherein purifying comprises diafiltering.

35. The method of claim 23, further comprising, after reducing with borane-pyridine complex, the step of:

purifying the conjugate into a pharmaceutically acceptable vehicle.

36. The method of claim 35, wherein the pharmaceutically acceptable vehicle is water including about 0.9% sodium chloride, water for injection including about 0.9% sodium chloride or lactated Ringer's solution.

37. The method of claim 23, wherein the amine is a chelator that is covalently bound to the water soluble carrier in the reacting step and the reacting step yields, a solution of the water soluble carrier comprising a concentration of covalently bound chelator of about 5 mM to about 200 mM.

38. The method of claim 37, wherein the concentration is about 80 mM to about 130 mM.

39. The method of claim 37, wherein the concentration is about 20 mM to about 30 mM.

40. The method of claim 37, wherein the concentration is about 35 mM to about 45 mM.

41. The method of claim 23, wherein total concentration of the water soluble carrier is about 5 g/L to about 250 g/L.

42. The method of claim 41, wherein the concentration is about 100 g/L to about 200 g/L.

43. The method of claim 1, wherein the Schiff base is formed from an amine and an aldehyde.

44. The method of claim 43, further comprising, before reducing the Schiff base, the step of:

forming the aldehyde by oxidizing a water soluble carrier to form a modified water soluble carrier comprising an aldehyde moiety.

45. The method of claim 2, wherein the reducing step reduces the Schiff base without substantially reducing the dialdehyde.

46. The method of claim 23, wherein the pH is about 4 to less than about 7.5.

47. The method of claim 23, wherein the pH is about 5 to about 6.

* * * * *